United States Patent [19]
Schwartz

[11] Patent Number: 6,089,869
[45] Date of Patent: Jul. 18, 2000

[54] LOW-DENSITY POLYETHYLENE DENTAL BLEACHING TRAYS

[76] Inventor: Dann A. Schwartz, 5504 Janice Ave., Kenner, La. 70065

[21] Appl. No.: 09/270,493

[22] Filed: Mar. 15, 1999

[51] Int. Cl.$^7$ ..................................................... A61C 5/00
[52] U.S. Cl. ........................... 433/215; 433/216; 433/80; 264/138
[58] Field of Search .................... 433/215, 41, 80, 433/6, 37, 42, 43, 71, 214, 216; 126/859, 860, 861; 264/138, 16, 219, 322, 339

[56] References Cited

U.S. PATENT DOCUMENTS

| | | | |
|---|---|---|---|
| 3,527,219 | 9/1970 | Greenberg | 433/215 |
| 4,044,762 | 8/1977 | Jacobs | 264/16 |
| 4,401,616 | 8/1983 | Wagner | 264/138 |
| 4,569,342 | 2/1986 | Von Nostitz | 433/48 |
| 5,076,791 | 12/1991 | Madray, Jr. | 433/215 |
| 5,112,225 | 5/1992 | Diesso | 433/48 |
| 5,692,894 | 12/1997 | Schwartz | 433/6 |
| 5,702,251 | 12/1997 | McClintock, II | 433/80 |

*Primary Examiner*—Gene Mancene
*Assistant Examiner*—Pedro Philogene
*Attorney, Agent, or Firm*—John M. Harrison

[57] ABSTRACT

Low-density polyethylene dental whitening or bleaching trays are molded to a dental impression cast of a patient, typically by vacuum or pressure thermoforming techniques. In a typical application, a low-density polyethylene plate or sheet is molded on a dental impression cast by operation of a vacuum or pressure thermoforming machine to produce bleaching trays of high quality and extended use for whitening the teeth of patients. The low-density polyethylene material so molded has superior memory for repetitive clinging fit on the teeth and is comfortable and virtually transparent while in place.

6 Claims, 1 Drawing Sheet

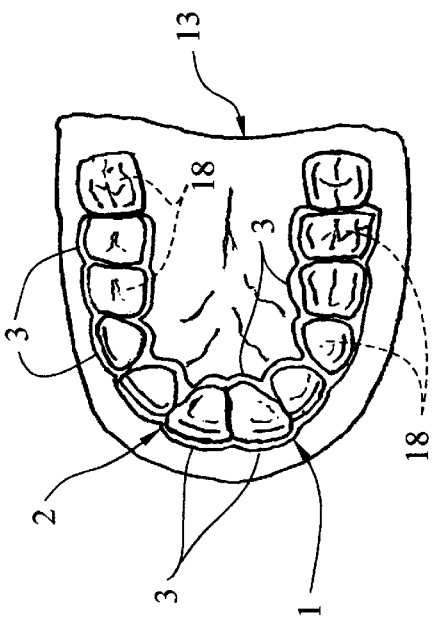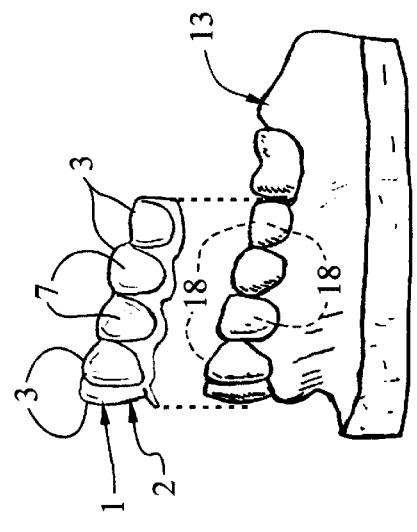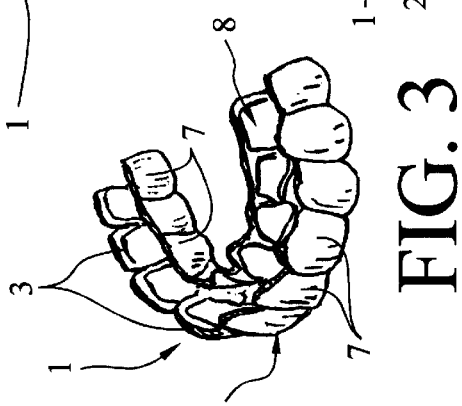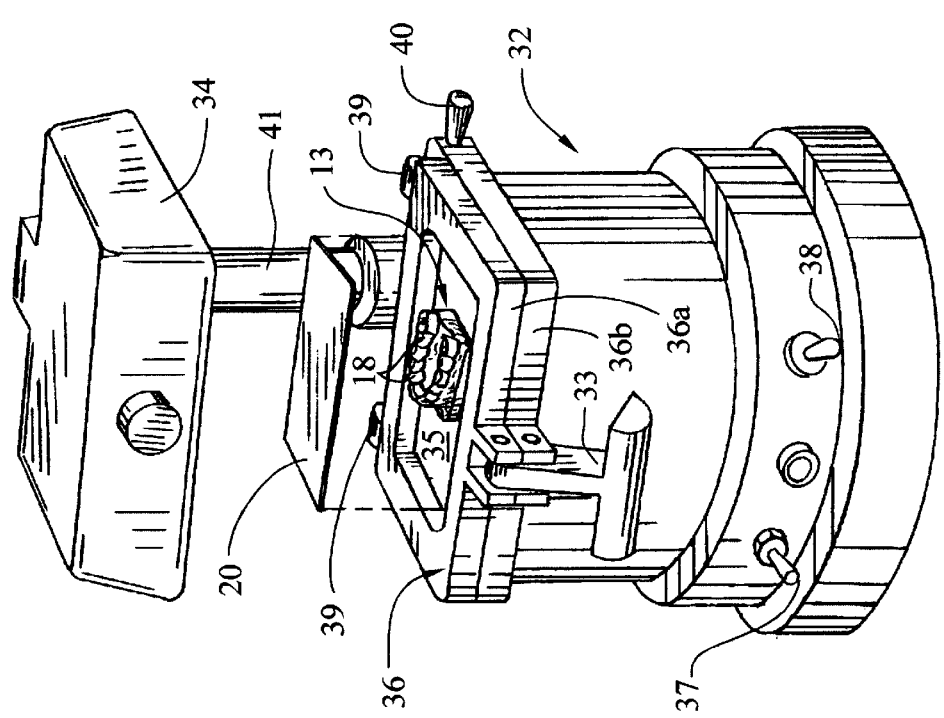

LOW-DENSITY POLYETHYLENE DENTAL BLEACHING TRAYS

BACKGROUND OF THE INVENTION

1. Field of the Invention

This invention relates to the molding of plastic whitening or bleaching trays used in the practice of dentistry and orthodontics. More particularly, the invention relates to low-density polyethylene bleaching trays which are typically shaped from a low-density polyethylene plate or sheet of selected thickness by a thermoforming machine, to the dental specifications of a patient, for bleaching the patient's teeth to a desired degree of whiteness. The low-density thermoplastic polyethylene material is characterized by substantial transparency and comfort when worn, along with resiliency, excellent memory and thus superior "clinging" fit, as well as excellent wear characteristics. The low-density polyethylene material also cools rapidly after shaping on the thermoforming machine, does not shrink, and is therefore virtually immediately ready for application to the patient's teeth as a bleaching appliance.

Various types of plastics are well known for use, typically with pressure or vacuum thermoforming machines, to construct such dental and orthodontic-related devices as dental bleaching trays. Typical of these materials in the "0.020 Coping"(polypropylene), a hard, thin, opaque material that has a low melting point and good thermo-forming characteristics and EVA 0.020–0.080 inches, a soft, semi-clear material which is easily vacuum-formed and trimmed.

Generic fit, disposable, plastic impression, whitening or bleaching trays are well known in the art, which trays are built to selected generic size specifications, but not to the exact specifications of a user's teeth. These trays are typically constructed of material such as ethyl vinyl acetate (EVA). However, the generic trays suffer from the disadvantage of failing to closely conform to the teeth of the patient and therefore sometimes facilitate a less than satisfactory uniformity in brightening the teeth, since the whitening gel does not always contact all portions or margins of the tooth surface as intended. Moreover, the EVA in sheet form is cloudy and tends to distort after vacuum or pressure forming and tends to impede a wearer's speaking ability. The sheet material EVA is also easily bitten-through by the user. Ethyl vinyl acetate and polypropylene (coping) are also used to vacuum mold bleaching trays, with varying degrees of patient satisfaction.

It has surprisingly been found that low-density polyethylene is a superb material for use in making dental whitening or bleaching trays and typically in the vacuum or pressure thermoforming of the impression or bleaching trays to the exact specifications of a patient. While generally thought to be too soft and opaque or white for application to the construction of dental appliances, and bleaching trays in particular, the thermoplastic low-density polyethylene tray is surprisingly comfortable to wear, nearly transparent and invisible when thinly molded and has good chemical resistance to both diluted and concentrated acids, peroxides, carbapoles, alcohols, aldehydes, bases and esters. Furthermore, although flexible, the low density polyethylene tray is tough and not easily bitten through and maintains its "memory" and structural integrity throughout a temperature range of from about −50 degrees centigrade to about 100-degrees centigrade and allows clear speech when worn, due to its thinness. The pressure or vacuum-formed low-density polyethylene material also fits snugly against the cervical third of the tooth and the clearance between the gingiva and the top edge of the tray can be closely controlled in the desirable range from no more than about 1 mm. to about 1.5 mm. Since this temperature range is ideal for the construction and use of custom-designed bleaching tray appliances from low-density polyethylene, the thermoplastic polyolefin material has been found to be ideal for such application. Low-density polyethylene sheets or plates for use in vacuum or pressure thermoforming bleaching trays according to this invention are typically shaped from the polymenzation of polyethylene at relatively high pressure and the translucent pellets can be shaped into the sheets or plates of selected thickness, typically from about 0.020 to about 0.040 of an inch, for thermoforming into bleaching trays. The material easily and efficiently accommodates state-of-the-art whitening agents, including hydrogen peroxide, carbomide peroxide and the like.

Low-density polyethylene is the first of the polyolefins originally prepared by the high pressure (100–500 atmospheres) polymerization of ethylene and its comparatively low-density arises from the presence of a small amount of branching in the polymerized chain (only about 2% of the carbon atoms), which gives a more open chain structure. While the material is comfortable to wear and is normally translucent-to-opaque in color, it has further surprisingly been found that it becomes substantially transparent at thicknesses of about one-third of a millimeter, after being thermoformed on a dental impression cast to the specifications of the teeth of a patient. The material is, at the same time, tough and flexible and has excellent "memory" to provide a good fit over the patient's teeth after thermoforming, without distortion of the material. Accordingly, the molded low density polyethylene bleaching tray is well suited to accept and uniformly distribute bleaching gel over the margins and surfaces of the teeth after the bleaching gel is applied to the interior surfaces of the tray.

In contrast to the desirable characteristics described above with regard to low-density polyethylene, the materials polypropylene and ethylvinylacetate, two materials which are commonly used to mold dental bleaching trays, are less desirable. These materials present minimal "memory" and barely acceptable fit over time in positioning on and removing from a patient's teeth. While polypropylene is able to withstand higher temperatures than low-density polyethylene, its rigidity makes it much less suitable for repetitive fitting than low-density polyethylene for application to dental bleaching trays.

Accordingly, it is an object of this invention to provide a new and improved "user friendly" thermoplastic low-density polyethylene for molding into dental bleaching trays.

Another object of the invention is to provide a new and improved low-density polyethylene sheet or plate material of selected thickness for vacuum or pressure thermoforming on a dental impression and creating a plastic bleaching tray which conforms to the dental impression and accurately, comfortably and repetitively fits the teeth of a patient and may be self-applied.

Still another object of this invention is to provide a new and improved low-density polyethylene thermoplastic material which may be manufactured in sheets of sufficient thickness for molding in a pressure or vacuum thermoforming machine and production of custom-made bleaching trays.

A still further object of this invention is to provide a new and improved low-density polyethylene plastic which may be shaped into thin plastic plates or sheets for use in pressure or vacuum thermoforming machines, where the sheets are heat and vacuum-molded over custom-made dental impression casts for creating high quality dental bleaching trays that closely and comfortably match the contour and configuration of a patient's teeth and are substantially transparent as so molded.

SUMMARY OF THE INVENTION

These and other objects of the invention are provided in a new and improved low-density polyethylene whitening and bleaching tray, typically shaped by vacuum or pressure thermoforming sheets or plates of low-density polyethylene by application of heat and vacuum to accurately conform to a dental impression cast of a patient. The product includes resilient, transparent, comfortable and flexible dental bleaching or whitening trays having an excellent close tolerance and an excellent "memory" and clinging fit, for repetitively positioning on the patient's teeth and uniformly applying a bleaching gel to the teeth for whitening the teeth in an optimum manner.

BRIEF DESCRIPTION OF THE DRAWING

The invention will be better understood by reference to the accompanying drawing, wherein:

FIG. 1 is a perspective view of a conventional vacuum thermoforming device for shaping the low density polyethylene bleaching trays of this invention;

FIG. 2 is a top view of a dental impression or cast with a low-density polyethylene bleaching tray heat and pressure-molded thereon;

FIG. 3 is a perspective view of the low-density polyethylene bleaching tray removed from the dental impression illustrated in FIG. 1; and FIG. 4 is a side view of the low-density polyethylene bleaching tray extended from the dental impression illustrated in FIG. 1.

DESCRIPTION OF THE PREFERRED EMBODIMENTS

Referring initially to FIGS. 1 and 2 of the drawing, a low-density polyethylene bleaching tray 1 (FIG. 2) having a tray body 2 with tray tooth impressions 3, is molded to conform to a dental cast or impression 13 of a patient's teeth, typically by operation of the conventional vacuum thermoforming machine 32, illustrated in FIG. 1. The dental impression 13 is molded to conform to a patient's upper or lower anterior dentition and is typically sprayed with a mold release agent and placed on the perforated vacuum plate 35 of the thermoforming machine 32, while a sheet or plate of low-density polyethylene 20 is positioned adjacent to the heating unit 34 of the thermoforming machine 32, as further illustrated in FIG. 1 and hereinafter more particularly described. Accordingly, the low-density polyethylene tray body 2 is formed on the dental impression 13 by first energizing the heating unit 34 of the vacuum thermoforming machine 32 by means of the heater switch 37. The dental impression 13 is then adjusted on the perforated vacuum plate 35 of the base 33 as illustrated in FIG. 1, with the cast teeth 18 of the dental impression 13 facing upwardly. Before the frame 36 is raised on the frame post 41 by means of frame lift knobs 40 to within a suitable heating distance of the heating unit 34, the top frame member 36a is pivoted upwardly on the hinges 39 with respect to the bottom frame member 36b and the thermoformable low-density polyethylene plastic plate 20 is centered on the bottom frame member 36b. The top frame member 36a is then pivoted downwardly and secured by means of the frame latch knob 33 and the frame 36 is raised on the frame post 41 using the frame lift knobs 40, such that the thermoformable low-density polyethylene plastic plate 20 is located immediately beneath the heating unit 34. After approximately 25 seconds of heating, the thermoformable low-density polyethylene plastic plate 20 is raised to a suitable thermoforming temperature and begins to flatten. The heating element is then turned off and pivoted from the position over the dental impression 13 and the vacuum motor (not illustrated) in the base 33 is then energized automatically or manually by means of the vacuum motor switch 38. The frame 36 is then rapidly lowered on the frame post 41 over the vacuum plate 35 by means of the frame lift knobs 40, such that the softened low-density polyethylene thermoforming plastic plate 20 is first draped, and then tightly vacuum-pulled over the cast teeth 18 of the dental impression 13. After about 30 seconds, the tray body 2 has been formed from the low-density polyethylene thermoformable plastic plate 20 positioned over the dental impression 13 as illustrated in FIG. 2. The molded tray body 2 may then be removed from the dental impression 13 and trimmed, after the tray body 2 has cooled to room temperature, which requires a time period of about one to two minutes.

Referring now to FIGS. 2–4 of the drawing, the low-density polyethylene bleaching tray 1 is illustrated as molded to the configuration of the dental impression 13 using the vacuum thermoforming machine 32, as described above. The low-density polyethylene bleaching tray 1 as so molded is characterized by the resilient tray body 2, which defines tray tooth impressions 7, bordering an impression cavity 8, which tooth impressions 7 closely match the cast teeth 18 (FIGS. 1 and 2) respectively, of the upper or lower dental impression 13. Bleaching gel (not illustrated) can be easily applied to the lingual surfaces of the tray tooth impressions 7, such that the low-density polyethylene bleaching tray 1 may be inserted over the upper or lower front teeth of a user and the bleaching gel operates to whiten the teeth.

Referring again to FIGS. 2–4 of the drawing, it will be appreciated by those skilled in the art that the low-density polyethylene bleaching tray 1 which is thermoformed from the low-density polyethylene plate 20 is characterized by a thickness which ranges from about 0.250 to about one-millimeter and preferably, about one-half of a millimeter. At this thickness, the low-density polyethylene is substantially transparent and is characterized by superior "memory" and flexibility, which facilitates very favorable repetitive clinging fitting over a user's teeth. Accordingly, the resiliency and flexibility of the low-density polyethylene material advantageously facilitates repetitive installation and removal of the low-density polyethylene bleaching tray to and from the teeth as necessary by a patient, to facilitate the desired whitening of the user's teeth. Another advantage of the low-density polyethylene material utilized in this invention is the rapid cooling of the low-density polyethylene bleaching tray 1 after removal of the dental impression 13 from the thermoforming machine 32. This characteristic facilitates the production of multiple low-density polyethylene bleaching trays in a short period of time, as the appliances can be quickly and easily removed from the cast teeth 18 of the dental impression 13 with minimum cool-down time, which prevents distortion of the trays.

The low-density polyethylene bleaching tray 1 is much improved over the disposable impression trays that are currently available on the market, in part because of the close fit between the tray tooth impressions 7 of the low-density polyethylene bleaching tray 1 to the cast teeth 18 of the dental impression 13, and thus the teeth of the patient, thereby facilitating a uniform application of bleaching gel to the teeth and uniform whitening of the teeth across all margins of the teeth.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A removable bleaching tray for wearing on a dentition and accepting a bleaching gel and bleaching the teeth on the dentition, comprising a low-density polyethylene tray body for receiving the bleaching gel, said tray body having a plurality of tooth impressions for receiving the respective teeth of the dentition and bleaching the teeth responsive to contact of the teeth with the bleaching gel provided in said tray body.

2. The removable bleaching tray of claim 1 wherein said tooth impressions comprise impressions of at least the canine, lateral incisor and control incisor teeth of the dentition.

3. A removable bleaching tray shaped from a molded dental impression and wearing on a dentition corresponding to the molded dental impression and accepting a bleaching gel for bleaching the teeth on the dentition, said bleaching tray comprising a low-density polyethylene tray body of selected thickness for receiving the bleaching gel, said tray body having a plurality of tooth impressions for receiving the respective teeth of the dentition and bleaching the teeth responsive to contact of the teeth with the bleaching gel.

4. The removable bleaching tray of claim 3 wherein said tooth impressions comprise impressions of at least the canine, lateral incisor and control incisor teeth of the dentition.

5. A method of whitening the teeth of a patient's dentition, comprising the steps of constructing a dental impression cast of the dentition; forming from said dental impression cast a low-density polyethylene bleaching tray body having a plurality of tooth impressions for receiving respective teeth of the dentition; and applying a bleaching gel to said bleaching tray body for contacting and whitening the respective teeth of the dentition responsive to insertion of said bleaching tray body on the respective teeth of the dentition.

6. The method of claim 5 wherein said dental impression comprises tooth impressions of at least the canine, lateral incisor and central incisor teeth of the upper dentition.

* * * * *